United States Patent
Sabin

(10) Patent No.: US 12,083,040 B1
(45) Date of Patent: *Sep. 10, 2024

(54) TOPICALLY APPLIED HEAT/THERMAL THERAPY FOR SKIN LESIONS AND OTHER DISEASES

(71) Applicant: Robert Sabin, Mill Neck, NY (US)

(72) Inventor: Robert Sabin, Mill Neck, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/600,704

(22) Filed: Mar. 9, 2024

Related U.S. Application Data

(63) Continuation-in-part of application No. 18/432,843, filed on Feb. 5, 2024, now Pat. No. 12,004,993, which (Continued)

(51) Int. Cl.
*A61F 7/12* (2006.01)
*A61F 7/00* (2006.01)
*A61F 7/02* (2006.01)

(52) U.S. Cl.
CPC ...... *A61F 7/007* (2013.01); *A61F 2007/0002* (2013.01); *A61F 2007/0018* (2013.01); *A61F 2007/0052* (2013.01); *A61F 2007/006* (2013.01); *A61F 2007/0072* (2013.01); *A61F 2007/0078* (2013.01); *A61F 2007/0086* (2013.01); *A61F 2007/0087* (2013.01); *A61F 2007/0093* (2013.01); *A61F 2007/0095* (2013.01); *A61F 2007/0282* (2013.01)

(58) Field of Classification Search
CPC ........ A61F 2007/0052; A61F 2007/006; A61F 2007/0086; A61F 2007/0087; A61F 2007/0093

See application file for complete search history.

(56) References Cited

U.S. PATENT DOCUMENTS

| | | | |
|---|---|---|---|
| 10,905,585 B1 * | 2/2021 | Sabin | A61M 16/0875 |
| 11,234,861 B2 | 2/2022 | Sabin | |
| 2021/0069011 A1 * | 3/2021 | Catalano | A61F 7/0085 |

OTHER PUBLICATIONS

Amazon.Com: Cordless Heat Gun for Milwaukee 18V Battery, MTIOLHIG Portable 112°F to 1022°F Battery Powered Heat Shrink Gun with 5pcs Nozzles for Crafts, Shrink Tubing, Vinyl Wrap, Paint Removal, www.amazon.com/Cordless-Milwaukee-Battery-Mtiolhig-Portable/dp/B0C2V6RCSS. 2024. 4 pages.

(Continued)

*Primary Examiner* — Tigist S Demie
(74) *Attorney, Agent, or Firm* — Alfred M. Walker

(57) ABSTRACT

A heat/thermal treatment is topically applied to skin lesions, skin cancers, metastatic cancer to the skin, other cancers, abnormal pre-cancer dysplasia cells, bacterial, fungal, viral, parasitic and other pathogens on or below the skin or skull. Insect borne diseases such as cutaneous leishmaniasis includes the topical administration of temperature controlled hot air to the skin or skull, or below the skin or skull, or directly to an internal lesion of an infected patient, with a concentrated heat source to an open outlet to raise the skin lesion temperature to a temperature capable of destroying pathogens causing cutaneous leishmaniasis and/or other viral, bacterial, fungal, parasitic or other diseases on or below the skin or skull of a patient. The invention may be administered within the body of the patient if the interior of the body is exposed during surgery.

12 Claims, 5 Drawing Sheets

Related U.S. Application Data is a continuation-in-part of application No. 18/418,179, filed on Jan. 19, 2024.

(56) References Cited

OTHER PUBLICATIONS

"The Disease | Dermato Therma." Dermato Therma, www.dermatotherma.com/the-project. 2024. 2 pages.
"Home | DermatoTherma." DermatoTherma, www.dermatotherma.com/. 2024. 4 pages.
"The Technology | Dermato Therma." Dermato Therma, www.dermatotherma.com/the-technology. 2024. 2 pages.
Gonçalves, Sheila Viana Castelo Branco, and Carlos Henrique Nery Costa. "Treatment of Cutaneous Leishmaniasis with Thermotherapy in Brazil: An Efficacy and Safety Study." Anais Brasileiros de Dermatologia, Sociedade Brasileira de Dermatologia, doi.org/10.1590/abd1806-4841.20186415. 2024. 9 pages.
Siadat, Amir Hossein et al. "Heat therapy for cutaneous leishmaniasis: A literature Review." Journal of research in medical sciences (JRMS) : the official journal of Isfahan University of Medical Sciences vol. 26 15. Feb. 27, 2021, doi: 10.4103/jrms.JRMS_934_19. 15 pages.
Kamink, Suzette, et al. "Failure of an Innovative Low-Cost, Noninvasive Thermotherapy Device for Treating Cutaneous Leishmaniasis Caused by Leishmania Tropica in Pakistan." AJTMH, The American Society of Tropical Medicine and Hygiene, Dec. 4, 2019, doi.org/10.4269/ajtmh. 19-0430. 16 pages.
Master ProHeat® Gun Kit—"ProHeat® 1400A LCD Digital Professional Heat Gun & Kit." Master Appliance Heat Tools, www.masterappliance.com/proheat-1400a-lcd-digital-professional-heat-gun-kit/#&gid=1&pid=2. 2024. 2 pages.
Master ProHeat® Nozzles—"ProHeat® 1400A LCD Digital Professional Heat Gun & Kit." Master Appliance Heat Tools, www.masterappliance.com/proheat-1400a-LCD-digital-professional-heat-gun-kit/#&gid=1&pid=2. 2024. 1 page.
Master ProHeat® Instructions—"ProHeat® 1400A LCD Digital Professional Heat Gun & Kit." Master Appliance Heat Tools, www.masterappliance.com/proheat-1400a-lcd-digital-professional-heat-gun-kit/#&gid=1&pid=2. 2024. 2 pages.
Milwaukee Heat Gun Accessories—Amazon.Com, www.amazon.com/Cordless-Milwaukee-Battery-Mtiolhig-Portable/dp/B0C2V6RCSS. 2024. 1 page.
Milwaukee Heat Gun Computer Display—Amazon.Com, www.amazon.com/Cordless-Milwaukee-Battery-Mtiolhig-Portable/dp/B0C2V6RCSS. 2024. 1 page.
Amazon.Com: Heat Gun Nozzle Attachments TOPINCN Shrink Wrap Hot Air Gun Accessories Tools Kit 7Pcs, www.amazon.com/Nozzle-Attachments-TOPINCN-Shrink-Accessories/dp/B07GDM6SDW. 2024. 1 page.
Milwaukee Heat Gun Safety Lock—Amazon.Com, www.amazon.com/Cordless-Milwaukee-Battery-Mtiolhig-Portable/dp/B0C2V6RCSS. 2024. 1 page.
"Hyperthermia to Treat Cancer." National Cancer Institute, www.cancer.gov/about-cancer/treatment/types/hyperthermia. 2024. 6 pages.
Nolen, Stephanie. "New Hope—and an Old Hurdle—for a Terrible Disease with Terrible Treatments." The New York Times, The New York Times, Dec. 19, 2023, www.nytimes.com/2023/12/19/health/leishmaniasis-fly-treatment-colombia.html. 9 pages.
"Four Latin American Countries Use Thermotherapy to Treat Cutaneous Leishmaniasis in Vulnerable Populations." PAHO/WHO | Pan American Health Organization, Dec. 18, 2023, www.paho.org/en/news/18-12-2023-four-latin-american-countries-use-thermotherapy-treat-cutaneous-leishmaniasis. 4 pages.
"Cutaneous Leishmaniasis: Swiss Students Develop Innovative Thermotherapy Device for Safer Treatment of 'Flesh-Eating Parasite.'" Drugs for Neglected Diseases Initiative (DNDi), Mar. 16, 2023, dndi.org/stories/2023/swiss-students-develop-innovative-thermotherapy-device-safer-treatment-cutaneous-leishmaniasis/. 5 pages.
Yetman, Daniel. "Hyperthermia Cancer Treatment: Uses, Procedure, Effectiveness,." Healthline, Healthline Media, Nov. 9, 2022, www.healthline.com/health/cancer/hyperthermia-cancer-treatment. 9 pages.
Zischke, Gena. "Thermosurgery Technologies | Brochure." Thermosurgery Technologies, www.thermosurgery.com/. 2024. 7 pages.
Berrcom Non-Contact Infrared Thermometer. 2024. 1 page.
Blaser, Sara. "The Social Impact Is Our Main Focus." Impact Zhaw, Jun. 27, 2023, impact.zhaw.ch/en/article/the-social-impact-is-our-main-focus. 6 pages.
Cardona-Arias, Jaiberth Antonio, et al. "Efficacy of Thermotherapy to Treat Cutaneous Leishmaniasis: A Meta-Analysis of Controlled Clinical Trials." PLOS ONE, Public Library of Science, May 26, 2015, doi.org/10.1371/journal.pone.0122569. 15 pages.
Reithinger, R., et al. "Efficacy of Thermotherapy to Treat Cutaneous Leishmaniasis Caused by Leishmania Tropica in Kabul, Afghanistan: A Randomized, Controlled Trial." OUP Academic, Oxford University Press, Apr. 15, 2005, academic.oup.com/cid/article/40/8/1148/320265. 8 pages.
López, Liliana, et al. "Thermotherapy. An alternative for the treatment of American cutaneous leishmaniasis." Trials vol. 13 58. May 17, 2012, doi: 10.1186/1745-6215-13-58. 15 pages.
Master ProHeat STC® —Surface Temperature Control Heat Gun Description 2024. 4 pages.
Master ProHeat STC® —Surface Temperature Control Heat Gun Summary 2024. 9 pages.
Master ProHeat STC® —Surface Temperature Control Heat Gun Specification/Instructions 2024. 11 pages.
Garza-Tovar, Talissa F.—An Overview of The Treatment of Cutaneous Leishmaniasis—Faculty Opinions. 2024. 9 pages.
Amazon.Com: RISWOJOR Laser Thermometer Non-Contact Digital Temperature Gun. https://a.co/d/fVfWEeT. 2024. 1 page.
"ThermoMed Treatments." Thermosurgery Technologies, www.thermosurgery.com/treatments. 2024. 3 pages.
ASTM-C1055_"Too-Hot-to-Handle"_JM-Editors_Standard_Guide_For_Heated_System_Surface_Conditions_that_Produce_Contact_Burn_Injuries_2015_6-pages.
OXO_SoftWorks_Magnetic-All-Purpose-Clips_one-page_photograph_2024.
The_Lancet_Leishmania:an_urgent_need_for_new_treatments_thelancet.com-vol. 87-January-2023_2-pages.
Refai-etal_Am_J_Trop_Med_Hyg_Vol-97-4_2017_pp-1120-1126_nih.

\* cited by examiner

Fig. 1
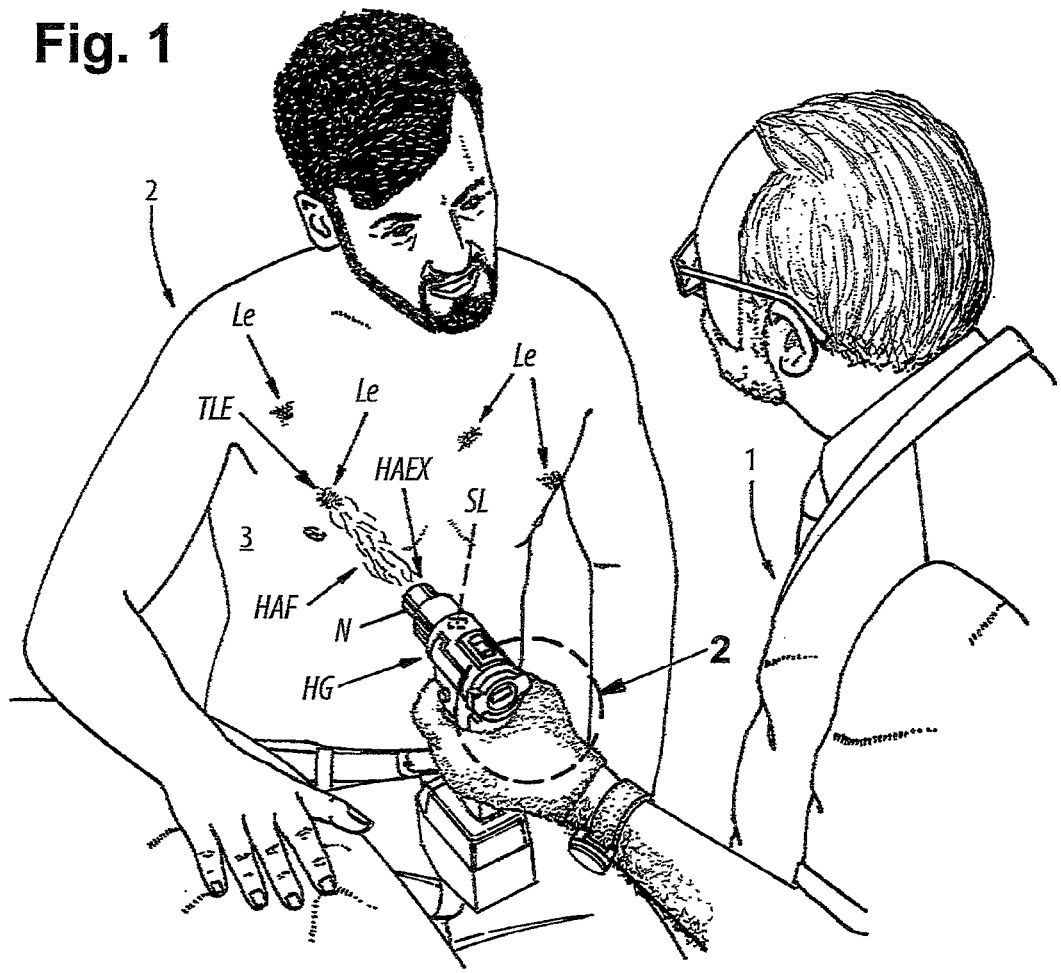
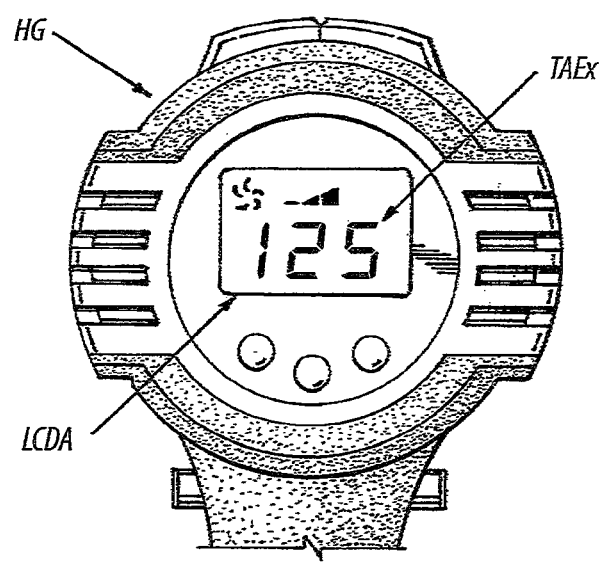
Fig. 2

TOPICALLY APPLIED HEAT/THERMAL THERAPY FOR SKIN LESIONS AND OTHER DISEASES

RELATED APPLICATIONS

This application is a continuation-in-part of application Ser. No. 18/432,843, filed Feb. 5, 2024, which '843 application is a continuation-in-part of application Ser. No. 18/418,179, filed Jan. 19, 2024, which '843 and '179 applications are incorporated by reference herein. Applicant claims priority under 35 U.S.C. § 120 from the '843 and '179 applications.

INCORPORATION BY REFERENCE

This application incorporates by reference in its entirety Applicant's U.S. Pat. No. 11,234,861 B2 issued Feb. 1, 2022, entitled RESPIRATORY THERAPEUTIC ELECTRIC HEAT SOURCE FACE MASK, and which '861 Patent was filed under USPTO application Ser. No. 17/337,352 on Jun. 2, 2021, which '352 application was published as US 2021/0282964 A1 on Sep. 16, 2021. This application also incorporates by reference in its entirety Applicant's U.S. Pat. No. 10,905,585 B1 issued Feb. 2, 2021, entitled RESPIRATORY THERAPEUTIC ELECTRIC HEAT SOURCE FACE MASK, and which '585 Patent was filed under USPTO application Ser. No. 16/893,212 on Jun. 4, 2020.

FIELD OF THE INVENTION

The present invention relates to topically applied heat/thermal therapy for skin and other lesions, such as Cutaneous Leishmaniasis and other protozoal caused diseases, skin carcinomas, and other cancers, abnormal pre-cancer dysplasia cells, fungal, and bacterial, viral, parasitic, infections, metastatic cancers on the skin or beneath the skin, or on or below the skull. For example, this invention relates to an improved heat treatment for Cutaneous Leishmaniasis, whereby the skin lesions of a patient are heated to a predetermined skin temperature, which is monitored in real time, during the topically applied heat/thermal therapy so that the skin is only heated to the required skin temperature needed to inactivate the pathogens or other invasive cells causing the skin lesions.

BACKGROUND OF THE INVENTION

All references are included in their entirety as if reproduced in full herein.

Cutaneous Leishmaniasis is an abhorrent disease which represents a huge unmet medical need. See the New York Times: "New hope—and an Old Hurdle—for a Terrible Disease With Terrible Treatments" by Stephanie Nolen, nytimes.com/2023/12/19/health/leishmaniasis-fly-treatment-colombia.html. This article reports cure of cutaneous leishmaniasis in a few days with heat therapy/thermotherapy like the applicant, applied locally, but without the harsh side effects of administering radiofrequency (RF) to heat the skin lesion with uncomfortable effects of heated electrodes contacting the skin lesion needing treatment.

See also DermatoTherma website "Cutaneous Leishmaniasis:" at dermatotherma, com/the-project, with geographic and numerical statistics about the prevalence, and demographics of Cutaneous Leishmaniasis. For example, see the DermatoTherma website "Using Radiofrequency energy for targeted heat therapy," at dermatotherma.com/the-technology. See also the DermatoTherma website "Providing treatment to the most neglected," at dermatotherema.com.

See the article "Cutaneous Leishmaniasis: Swiss students develop innovative thermotherapy device for safer treatment of 'flesh-eating parasite,' at-safer-treatment-cutaneous-leishmaniasis/dndi.org/stories/2023/swiss-students-develop-innovative-thermotherapy-device/.

See National Cancer Institute "Hyperthermia to treat cancer," at cancer.gov/about-cancer/treatment/types/hyperthermia. NCI discloses that temperature at about 113° F. kills cancer cells with little or no harm to normal human body tissue. The New York Times, opus cited, at page 3/9, discloses that treating human tissue topically at 50° C., for 30 seconds 122° F., kills the parasite/Leishmaniasis protozoa deep inside the human tissue.

See also "Heat therapy for cutaneous Leishmaniasis: a literature review" by Amir Hossein Siadat et al in the Journal of Research in Medical Sciences, at ncbi.nlm.nih.gov/pmc/articles/PMC8106408/#:-text=, which states, "we reviewed all of the articles in PubMed regarding the use of heat therapy for the treatment of CL that were comparable to meglumine antimony." This review discloses that heat therapy through various means (but not including hot air as Applicant describes) kills the Cutaneous Leishmaniasis parasite. Delivery of heat was accomplished using hot water baths, ultrasound, radio frequency i.e., DermatoTherma RF machine, ThermoMed RF machine, FDA approved, for the treatment of Cutaneous Leishmaniasis since 2007, using infrared and microwave, and handheld exothermic crystallization thermotherapy.

Additionally, Garza-Tovar, Talissa F., et. al. describes "an overview of the treatment of cutaneous Leishmaniasis" such as cutaneous, visceral, mucocutaneous presentations, and other drug and related treatments in Faculty Opinions 2024. Garza-Tovar specifically discusses local and intralesional therapies such as antimonials combined with cryotherapy, heat therapy with infrared lights, laser, or direct electrical stimulation, or radio frequency waves, at 50 degrees Centigrade (122 degrees Fahrenheit), topical paromomycin, antifungals, immunomodulators, and other alternative treatments.

See also Goncalves et al, "Treatment of cutaneous Leishmaniasis with thermotherapy in Brazil: an efficiency and Safety Study" in An. Bras. Dermayol. 1.93 (3) May-June 2018. In this study, Radio Frequency based thermotherapy was used on patients in the same temperature of about 122° F. This paper shows that topical application of heat works in treating Cutaneous Leishmaniasis.

See also Pan American Health Organization (PAHO), "Four Latin American countries use thermotherapy to treat cutaneous leishmaniasis in vulnerable populations", Paho.org/en/news/18-12-2023. The thermotherapy is described as using "high frequency waves" topically applied at 50° Celsius for 30 seconds.

See also Daniel Yetman, "Hyperthermia Treatment for Cancer: Uses and Effectiveness", Healthline Newsletter, Nov. 9, 2022 (reviewed by Teresa Hagan Thomas). Yetman discloses that temperatures of 106° F. to 111° F. are toxic to cancer cells while sparing normal cells.

There are severe faults with the aforementioned radiofrequency (RF) technologies, such as the DermatoTherma RF Device, or the ThermoMed 1.8 device. For example, the two electrodes are close together and placed on the skin. See DermatoTherma Disclosure, Using Radiofrequency Energy for targeted Heat Therapy, opus cited, so that not a lot of skin lesion area is covered by the small electrodes.

See Drugs for Neglected Diseases Initiative (DNDi) "Cutaneous leishmaniasis: Swiss students develop innovative thermotherapy device for safer treatment of "flesh-eating parasite, which describes radiofrequency (RF) electrode use. However, Applicant notes that for a large lesion, this requires repetitive movement of the electrodes on and around the lesion. See DNDi, where the problems of CL lesions may not lend themselves to the DermatoTherma RF device and the ThermoMed device, as the electrodes are small and if the lesions are large, multiple uses of the electrodes may be required. See DermatoTherma Technology, "Using Radiofrequency Energy for Targeted Heat Therapy", about the size of electrodes in RF heat therapy devices. The DNDi literature discloses secondary burns with the electrode lying on the lesion. Another fault is that there is no positive pressure from the electrodes to drive the heat into the lesion. Another possible flaw of RF electrode devices is that by being compelled to move the electrodes/ heat source around the lesions, there will be a variability of temperature in the tissues being treated by RF frequency. Furthermore, according to the Applicant herein, because of the severe toxicity of the electrode lying on top of the lesion, and interfacing with the lesion, the maximum temperature that can be used is 122° F.

Clearly, Applicant overcomes this flaw of electrodes in RF devices not being able to heat the affected skin lesion more than 122° F., by being able to provide higher temperatures, i.e. at 132° F. or more, would provide better, quicker, safer, less toxic results because Applicant does not apply small electrodes directly to the skin lesion, but instead remotely applies heated air, which is less severe than direct electrode heating of the skin lesion, while monitoring the temperature of the skin lesion, so that it falls within a temperature threshold required to inactivate the CL parasites at the skin lesion.

The ThermoMed RF machine has been used in many published trials, see Table 1, Siadat op cit, page 5. The efficacious dose in mostly all of these trials is single administration of electrode-producing radiofrequency at 122° F. for 30 seconds, at frequency of once weekly, or once total, mostly in a single administration of the RF heat to the skin lesion via electrodes. At least three devices have been used in these trials using (RF) techniques. See Table 1, Op cit.

All RF devices used have two electrodes which are handheld, as noted in the image of the ThermoMed device, DermatoTherma device. The RF electrodes touch and interface with the lesion, and are moved around the lesion.

Kämink, Suzette, et al. in "Failure of an Innovative Low-Cost, Noninvasive Thermotherapy Device for Treating Cutaneous Leishmaniasis Caused by Leishmania Tropica in Pakistan." AJTMH, The American Society of Tropical Medicine and Hygiene, 4 Dec. 2019, doi.org/10.4269/ ajtmh.19-0430, discloses that although the cure rate is between 54% and 94%, "The disadvantage is that the application with the ThermoMed is very painful. For this reason lidocaine 2% solution has to be injected around the lesions, before the TT session; otherwise the pain becomes unbearable for the required duration of 30 seconds also, secondary burns usually occur".

Moreover, Lopez et al, in "Thermotherapy, an Alternative for the Treatment for American cutaneous leishmaniasis", Trials. 2012; 13: 58. Published online 2012 May 17. doi: 10.1186/1745-6215-13-58, thermotherapy often resulted in failures with relapses 50% of the time, and local pain lasted for four days after initiating thermotherapy treatment at 50 degrees Celsius (122 degrees Fahrenheit) for thirty seconds.

OBJECTS OF THE INVENTION

It is therefore an object of the present invention to provide a concentrated heat source to an open tube/nozzle for destroying pathogens such as protozoa causing Cutaneous Leishmaniasis, other viral, bacterial, fungal and/or other pathogens causing skin cancers, and for destroying other diseases and pathogens on the skin, or under the skin or skull, including other cancers or abnormal pre-cancer dysplasia cells.

It is also very desirable to have a handheld, battery powered or powered by 120 V utility power heat gun with safety locks, operable for heat treatment of skin lesions in real time, which is way less toxic, less painful, more efficacious, quicker, operates at a higher temperature, and cost effective. Moreover, the higher temperatures available facilitate treatment of pathogens beneath the skin such as tumors, fungal, bacterial, viral, tick-borne diseases, insect ticks themselves, and farm animal pathogens, to name a few.

It is also an object to provide a cost-effective hot air machine, with 2 batteries, and where the charger cost is a small fraction of the cost of existing RF electrode-based machines, and without costly maintenance.

Other objects of the invention will become apparent from the following description of the present invention.

SUMMARY OF THE INVENTION

The present invention relates to topically applied heat/ thermal therapy for skin and other lesions, such as cutaneous Leishmaniasis, skin carcinomas, and other cancers, abnormal pre-cancer dysplasia cells, fungal, and bacterial, viral, parasitic, infections, metastatic cancers on the skin or beneath the skin, or on or below the skull. For example, this invention relates to an improved heat treatment for cutaneous Leishmaniasis, whereby the skin lesions of a patient are heated to a predetermined skin temperature, which is monitored during the topically applied heat/thermal therapy so that the skin is only heated to the required skin temperature needed to inactivate the pathogens or other invasive cells causing the skin lesions.

Applicant's novel hot air topical skin treatment is not cited in Siadat et al, opus cited, or any of the aforementioned literature articles incorporated by reference in their entirety herein.

In contrast to the aforementioned electrode based prior art methods of increasing skin lesion temperatures to destroy disease casing pathogens, such as those causing Cutaneous Leishmaniasis, see Applicant's U.S. Pat. No. 11,234,861 B2 "Respiratory Therapeutic Electric Heat Source Face Mask", dated Feb. 1, 2022, and its parent U.S. Pat. No. 10,905,585 B1 "Respiratory Therapeutic Electric Heat Source Face Mask", dated Feb. 2, 2021, which are both incorporated by reference herein in their entirety, for information about heated air sources, such as heat guns, with air temperature safety locks and interlocks providing controlled and monitored application of hot air into the respiratory system of a patient, without exceeding a predetermined safe temperature threshold of hot air. These heat guns disclosed in these patents can also be used, although they require a 120 Volt, plug in power supply.

To treat tumors under the skin, the Applicant's device can be placed directly over the skin and over the tumor without touching the skin. Applicant's invention never touches the skin, in contrast to the painful prior art electrodes. The method includes the steps of;

a) placing a concentrated gentle but efficacious exterior topically applied heated air generated by a heat source adjacent to and spaced from said cancer on and/or extending beneath said skin of said patient.
b) directing said gentle but efficacious exterior topically applied heated air from said heat source at said cancer on and/or extending beneath the skin and/or skull of a patient;
c) applying said gentle but efficacious exterior topically applied heated air directed from said heat source to a full area of said cancer on and/or extending beneath the skin and/or skull of a patient, without moving said heat source;
d) programming said heat source for producing and directing said gentle but efficacious exterior topically applied heated air having a temperature sufficient for, and for a sufficient time, to destroy said cancer on and/or extending beneath the skin and/or skull of a patient;
e) monitoring said heat source for insuring that said gentle but efficacious exterior topically applied heated air being delivered to said cancer on and/or extending beneath the skin and/or skull of a patient does not exceed a predetermined safe temperature threshold of said gentle but efficacious exterior topically applied heated air; and,
f) mounting a display on or adjacent said heat source showing said set programmed temperature and a current temperature at a skin surface located at or above said cancer being treated, said cancer located on and/or extending beneath the skin and/or skull of a patient.

The method further includes the heat source preferably being a heat gun with an outlet nozzle sufficiently large and shaped to cover all of the cancer, wherein a display on the heat gun comprises an LCD screen showing both of the temperatures, including the set programmed temperature and the current temperature at a surface at or above the cancer located on and/or extending beneath the skin and/or skull of a patient. The set programmed temperature is displayed on an upper portion of the screen and a current skin temperature at a surface at or above the cancer is displayed on a lower portion of the screen.

The method includes further using a laser infrared light beam projected on the skin surface located at or above the cancer for measuring the surface temperature of the skin located at or above the cancer, to determine inferentially the temperature of the cancer located at or below the surface of the skin or skull of the patient.

The heat gun has different sized nozzles for different sized cancers, wherein the gentle but efficacious exterior topically applied heated air is delivered to the cancer located at or below the surface of the skin or skull of the patient is in the range of about 107 to 113 deg. F.

Optionally, a masking template is employed to isolate unaffected skin area from the gentle but efficacious exterior topically applied heated air emanating from the heat gun, in which the outlet nozzle of the heat gun is centered over the cancer located at or below the surface of the skin or skull of the patient. Also optionally, Lidocaine is administered in a pre-procedural step to anesthetize the skin cancer located at or below the surface of the skin or skull of the patient and surrounding non-cancerous skin.

A further option includes the step of inserting a subcutaneous needle probe temperature monitor into the in situ site of the tumor beneath the skin being treated and measuring the temperature of the tumor being treated. Also optionally, there comprises the step of measuring the surface temperature of the skin located at or above the cancer, and determining inferentially the temperature of the cancer located at or below the surface of the skin or skull of the patient.

Because coffee and hot chocolate are served between 160° F.-185° F. of heat to billions of people for many decades without burning the mouth, then it is reasonable that Applicant's invention can be applied at 140+° F. of heat above the skin, over the tumor or cancer. At 140+° F., 32° F. of heat will be lost going down the skin to the tumor, leaving 108° F. of heat at the tumor site, which is toxic to tumor cells, and thus killing the tumor. In other words, a portal is established to supply cytotoxic heat to the tumor using the portal.

However, the American Society of Testing Materials (ASTM) recommends that skin contact with hot surfaces in industrial applications should preferable be about 140° F. at a duration of five seconds. See ASTM-C1055_"Too_Hot_to_Handle" JM-Editors_Standard-Guide-for-Heated-System-Surface-Conditions-That-Produce-Contact-Burn-Injuries_2015_6_pages.

Applicant has heard a number of times whereby a surgeon opens up a cancer patient's torso, and gasps nothing to be done, extensive disease, or looked at an x ray with the same conclusion. Now, with the applicant's invention, the surgeon can open a patient's chest, abdomen, etc., and using the applicant's invention, he can kill the tumors, cancer cells, abnormal pre-cancer dysplasia cells, pathogens of every kind, bacterial, viral, fungal, parasitic in a brief time, since 122° F. kills the Protozoa in 30 seconds, and 108° F. kills the tumor cells.

The method of Applicant's invention includes a temperature monitored application of hot air to the skin lesion, where the threshold temperature of the patient's skin lesion is measured and monitored by either built-in laser infrared temperature sensor features, or by remote handheld non-contact, infrared-based skin lesion thermometers during the procedure, in order to inactivate the pathogen causing the skin lesion. whereby a threshold temperature of the skin lesion inactivates the skin lesion causing pathogens.

The laser infrared beam from the non-contact temperature thermometer contacts the target of the heat gun at the skin lesion. The skin lesion temperature is impacted by the heated hot air of the heat gun, exactly at the point of impact on the skin lesion.

An example of a preferred embodiment for a heat gun, which uses nozzles for aiming monitored hot air flow, with built-in safety locks and interlocks, but which also has a built-in laser infrared temperature sensor and LCD display, is manufactured by Master Heat Tools, as MASTER PRO-HEAT STC®, which is a surface temperature control heat gun. This heat gun can dispense hot air to the skin lesion at specified exiting air temperatures, so that the skin lesion is treated at a predetermined skin lesion temperature to inactivate the CL pathogen.

Examples of an alternate embodiment includes a heat gun used with a separate remote handheld non-contact, infrared-based skin thermometers include the non-contact human skin thermometer of Berrcom. Additionally, industrial remote, handheld non-contact, infrared-based surface thermometers manufactured under the tradename Riswojor also can be used on the skin of the patient to measure the critical skin temperature for inactivation of pathogens such as protozoa (such as the phlebotomine sand fly bite borne protozoa, causing Cutaneous Leishmaniasis), viruses, cancer causing cells, abnormal pre-cancer dysplasia cells, fungi, and other bacterial pathogens.

The preferred range of the skin temperature being treated can be preferably in the range of about 110 degrees F. up to about 140+degrees F., such as 120 degrees F. to about 130 degrees F., which is the preferred skin temperature measured by the before mentioned prior art procedures with skin applied heated electrodes, needing topical lidocaine treatments that require the treated lesion skin to be 122 degrees F.

The Applicant's invention uses the aforementioned infrared based, non-contact thermometers, to remotely determine the skin temperature when the medical practitioner is holding a heat gun, which has a LCD display, but which only indicates the temperature of the heated air coming out of the heat gun, not the remote temperature of the skin lesion being treated.

Therefore, the drawings herein show one hand of the medical practitioner holding the heat gun, and the other hand would be holding an extension clamp of a template mask with holes to expose the region of the skin needing treatment. In order to avoid the practitioner having to put down the template to measure the skin temperature with the non-contact medical thermometer, preferably an assistant should be available to hold the non-contact skin thermometer during the procedure using the heat gun of the Applicant's invention. A suitable clamp is an OXO SoftWorks Magnetic All-Purpose Clip.

The present invention utilizes a heat gun, preferably battery powered, with a variable size opening nozzle set, or 120 Volt power if available. Applicant's invention utilizes a handheld laser infrared thermometer to add another layer of safety, to monitor temperature of the skin being treated in real time, during administration of the treatment. There are many battery powered heat guns available commercially on Amazon.

Applicant submits the following reference for incorporation by reference in its entirety, entitled "Cordless heat gun for Milwaukee 18v battery, Mtiolhig portable 112° F. to 1022° F. battery powered heat shrink gun with 5 pcs nozzles for crafts, shrink tubing, vinyl wrap, paint removal." There are also quick connect nozzle kits with many different size nozzles available on Amazon. This Mtiolhig heat gun machine overcomes three major drawbacks of the Thermomed RF machine, and Derma Thermato device and all RF skin electrode-based devices.

Namely, the present invention utilizes no electrodes to lie on top of the skin/lesion and move around, possibly causing the documented severe skin pain, with possible delayed pain and possible secondary skin burns, thus limiting the temperatures of the skin being treated. Second, the area of the heated air derived from the applicant's inventions covers the entire lesion, at one time, beginning to end, over the entire area of the skin lesion at one time, from beginning to end, without touching the skin lesion with a possible toxic electrode, negatively affecting the skin lesion, as well as possible secondary skin burns.

The present invention does not expose the skin lesion with unnecessary moving around with its inherent variability of temperature of the skin being treated.

In contrast, the present invention monitors and regulates the temperature of the skin being treated. The heated air flow of the Applicant's invention may be raised and lowered by pressing control buttons on the heat source, which is preferably a heat gun with built in safety locks to prevent inadvertent excess heat and air pressure being administered to the skin of the patient.

For example, Applicant's heat gun can be, preferably, battery powered and portable. If utility power such as 120 Volts is available, the heat gun can be powered by utility power as well.

The heat gun of the present invention can have a set of different quick-change nozzles for different size lesions, as well as auxiliary template masks with holes sized to expose only the affected area of the skin lesion being treated.

Applicant's heat gun may have adjustable six-speed air flow settings to adjust positive pressure of hot air on the lesion, therefore to drive the heat from the heat gun onto and into the skin lesion being treated.

Because the temperature of the skin lesion being treated is more important than the temperature of the heated air from the heat gun, Applicant's heat gun operates at about 120° F. to about 130° F., or higher, or lower, with an emphasis on higher, to achieve the preferred temperature of 122° F. for the skin being treated, where, in contrast, 122° F. is the maximum skin lesion temperature, produced by skin contact heated electrodes, as described in the prior art of the DermatoTherma heated electrode-based machine, and the ThermoMed heated electrode-based device.

Many published clinical trials with RF-based topical electrode heat machines have used the ThermoMed device, most at 122° F., generally a single dose at 30 seconds. In contrast, Applicant's topical heated air machine, without having electrodes touching the skin, can operate at higher temperatures of the skin being treated, i.e. 132F+, for example. The prior art heated electrode-based machines which touch, move, and stay on the skin may cause significant pain. The Applicant's heated air-based and temperature monitored system overcomes the difficulties of the prior art.

Because the DermatoTherma machine's electrodes, and the ThermoMed 1.8 device and other radiofrequency (RF) electrode-based devices rest on the lesion, the temperature of the skin being treated may not be easily raised for concern about burning. Already there are major secondary burns at 122° F. when RF signals are produced by skin contact electrodes of the prior art. In contrast, Applicant's heat gun is designed with a temperature locks, such as a button for safety, or other locks and interlocks described in Applicant's U.S. Pat. No. 11,234,861 B2 "Respiratory Therapeutic Electric Heat Source Face Mask", which is incorporated by reference herein in its entirety. See four enclosures in the attached Amazon reference for this heat gun, where the four enclosures show a heat gun, different nozzles and control buttons.

The proposed administration of applicant's invention herein includes the topical administration of temperature controlled hot air to the skin lesion, measured by the temperature of the skin of an afflicted patient, with a concentrated heat source to an open outlet tube, such as a flared or diminished distal end nozzle, for destroying pathogens such as protozoa causing cutaneous leishmaniasis, other viral and/or idiopathic pathogens causing skin cancers, and for destroying other diseases and pathogens on the skin, or below the skin The present invention can also treat cancers/tumors, abnormal pre-cancer dysplasia cells, bacterial, fungal, viral, parasitic infections, and other pathogens, beneath the skin, because it is possible to transfer enough heat to cancers beneath the skin, if the tumors are close enough to the skin to be responsive to the application of heat, since prior art heat provided directly to tumors at temperatures of the skin being treated to be 107° F.-113° F. kills cancerous tumors.

In the present invention, the topically applied hot air applied to the skin lesion of the patient is adjusted upward to a temperature of the skin lesion being treated controlled topically applied temperature of the skin being treated, which is adjusted upward from about 120° F. to about 130° F. to a temperature of the skin being treated at about 130° F.-190° F.

For narrow pin-point administration of the temperature of the skin lesion or other affliction, such as cancerous tumors, or abnormal pre-cancer dysplasia cells, for example, being treated and controlled by hot air flow, the diminished distal end nozzle can be used. Several round and assorted nozzles are provided for different size lesions. But where the affected area is large, extending over multiple stretched out or repetitive areas of skin, as is prevalent in Leishmaniasis, the flared open ended nozzle tubes can be utilized. As the clinician's preferred choice, The steps of the method of use of Applicant's invention include the step of providing Applicant's concentrated heat source to and through an open tube nozzle, topically to the affected skin lesion of a patient, for inactivating and destroying pathogens such as protozoa causing Cutaneous Leishmaniasis, other viral and/or pathogens causing skin cancers, abnormal pre-cancer dysplasia cells, and for destroying other diseases and pathogens on or below the skin.

In one embodiment, the method steps include the following:
  a) install a correct nozzle on the heat gun;
  b) determine and adjust the temperature of the skin being treated and airflow;
  c) administer pre-procedure Lidocaine to anesthetize the skin lesion and surrounding non-lesion skin;
  d) program and provide the heated hot air flow at a threshold temperature of the skin lesion sufficient to inactivate the pathogen causing the skin lesion;
  e) monitoring the temperature of the skin lesion;
  f) adjust the output nozzle of applicant's heat gun and supply hot air over the patient's skin having a Cutaneous Leishmaniasis lesion, tumor or other pathogen damaged tissue at an acceptable distance therefrom;
  g) activate the temperature-controlled heat gun with locks and interlocks, at which time the entire lesion will be contacted and contacted with heat derived from hot air at controlled threshold temperatures of the skin lesion being treated, without touching the skin or moving around the adjoining skin; and,
  h) retreatment may be done, subject to the clinician's call.

While the aforesaid example of a method is specific to one embodiment, in general, the present invention preferably includes a method of using heat therapy for treating Cutaneous Leishmaniasis, cancers and subcutaneous carcinomas subject to externally applied heat, abnormal pre-cancer dysplasia cells, viral, bacterial, fungal infections, tick-borne diseases, and other parasitic infections of the skin, and removing and/or killing live tick insects, comprising the steps of:
  a) placing a concentrated heated air source adjacent to and spaced from one or more lesions on the skin of a patient containing one of said parasitic infections or cancerous tumors, or abnormal pre-cancer dysplasia cells;
  b) programming and directing heated air from said heat source at said one or more lesions at a selected predetermined safe temperature, to achieve the preferred temperature of the skin lesion of the skin being treated, and at a selected safe air pressure;
  c) said heated air directed from said heat source being applied to a full area of at least one lesion of said one or more lesions without moving said heat source from said at least one lesion of said one or more lesion;
  d) said heated air directed from said heat source being sequentially applied to a full area of another lesion of said one or more lesions, and repeated for the remainder of said one or more lesions;
  e) said heated air source producing and directing said heated air to the skin of the patient, so that the skin of the patient has a temperature sufficient for, and for a sufficient time, to destroy pathogens in said at least one skin lesion; and
  f) monitoring the skin for ensuring that the skin does not exceed a safe temperature threshold of the skin.

BRIEF DESCRIPTION OF THE DRAWINGS

The present invention can best be understood in connection with the accompanying drawings, it is noted that the invention is not limited to the precise embodiments shown in the following drawings, in which:

FIG. 1 is a perspective view of a healthcare provider administering heated air to a lesion on the skin of a patient, where the temperature of the heat equals the temperature of the skin lesion being treated, not the temperature of the heat exiting from the heat gun.

FIG. 2 is a close-up detailed view of the LCD viewing screen, taken along dashed view circle line "2" of FIG. 1, showing the temperature of the exiting air from the heat gun through a nozzle pointed at the skin lesion.

FIG. 3 also shows a plurality of templates of varying area sizes, fitting to different sized skin lesions, whereby the area of the skin outside of the lesion is protected from direct contact with the exiting heat from the heat gun.

FIG. 5 also shows the healthcare practitioner holding the heat gun and a medical assistant holding a separate handheld non-contact surface temperature measuring device.

DETAILED DESCRIPTION OF THE INVENTION

Figures 3, 3A:
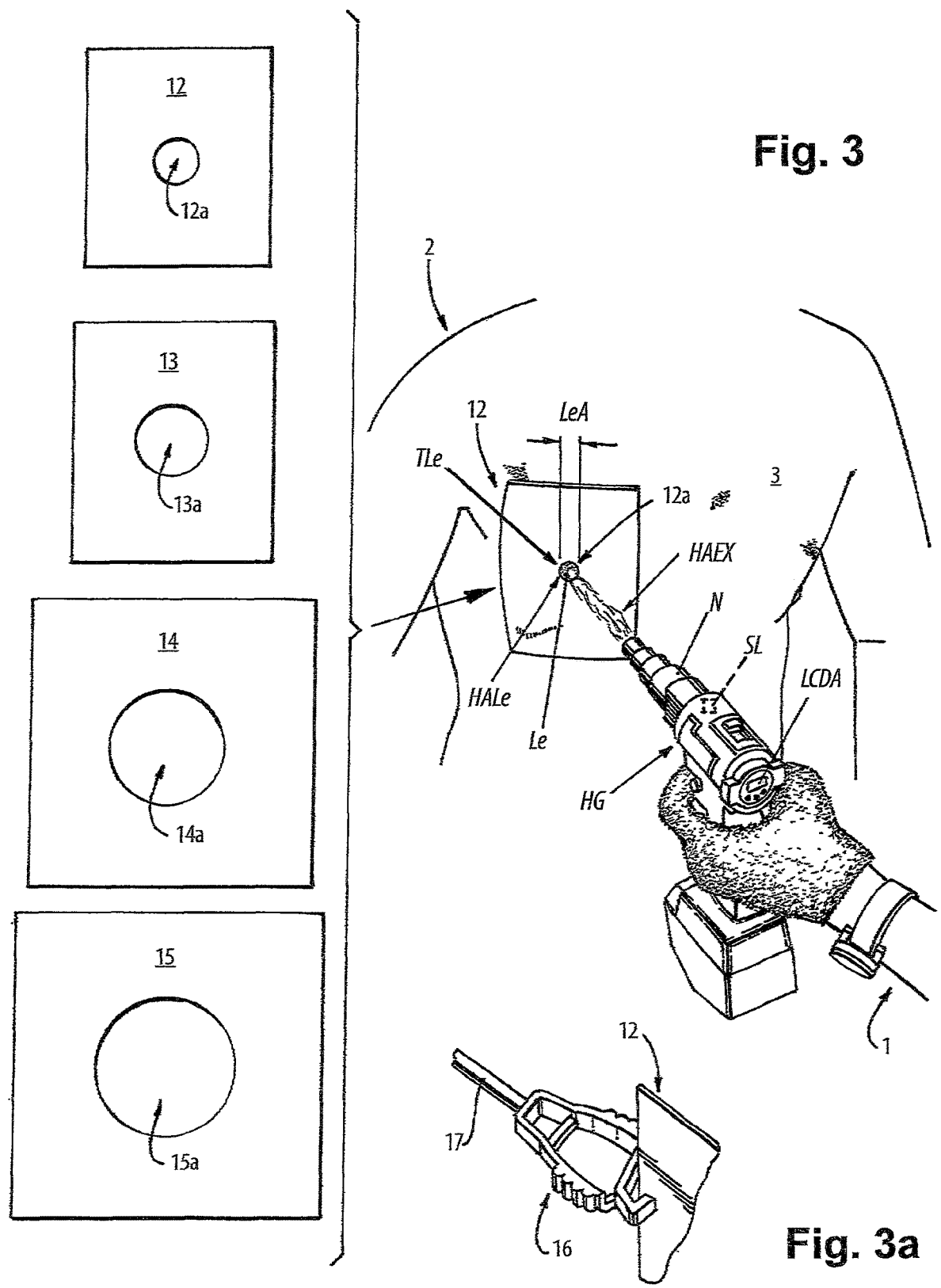
FIG. 3 is a front perspective view, as in FIG. 1, showing the healthcare provider administering heated air to a lesion on the skin of a patient, where the heat is limited to the area of a hole on a masking template, and the hole is configured to be limited to the area of the skin lesion.
FIG. 3a is a close-up detailed view of a clamp holding a masking template shown in FIG. 3, at the distal end of the clamp, whereby the proximal end (not shown) includes a rod handle for manual or stationary holding of the clamp and masking template.

The present invention has broad applications to many medical fields for a variety of therapeutic applications. However, it is particularly adapted for patients afflicted with skin afflicted lesions caused by pathogens. The drawings are for illustrative purposes only, and the preferred mode for carrying out the invention is described herein.

As used throughout this specification, the word "may" is used in a permissive sense (i.e., meaning having the potential to, or being optional), rather than a mandatory sense (i.e., meaning must), as more than one embodiment of the invention may be disclosed herein. Similarly, the words "include," "including," and "includes" mean including but not limited to.

The phrases "at least one," "one or more," and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that the citing of any reference within this disclosure, i.e., any patents, published patent applications, and non-patent literature, is not an admission regarding a determination as to its availability as prior art with respect to the herein disclosed and claimed apparatus/method. Furthermore, any reference made throughout this specification to "one embodiment" or "an embodiment" means that a particular feature or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

In connection with the present invention, the drawings show one or more embodiments, but the present invention is not limited to that shown in the drawings, in which FIG. 1 shows a healthcare provider 1 administering heated air flow HAF from heat gun HG at a first exiting temperature HAEX toward a lesion Le on the skin 3 of a patient 2, for a time period of about thirty (30) seconds, whereby in the thirty (30) second time duration, the higher temperature HAEX of the heated airflow HAF is slightly cooled down to a temperature TLe of the skin lesion Le being treated. Therefore, the reduced temperature TLe at the site of the skin lesion Le, is the actual temperature required to inactivate the pathogen causing the skin lesion Le, not the initial exiting temperature HAEX of the heated exiting air, exiting from the heat gun HG. A typical heat gun HG can be a Milwaukee cordless portable heat gun with an 18V battery, with assorted nozzles N. Optionally the heat gun can be corded to an AC outlet at 120V AC power. The heat gun HG also has built-in safety locks SL, such as disclosed in Applicant's U.S. Pat. No. 11,234,861 B2, issued Feb. 1, 2022, and Applicant's U.S. Pat. No. 10,905,585 B1, issued Feb. 2, 2021, to control the exiting heated air temperature HAEX to a predetermined lockable safe temperature for topical application to the skin 3 of a patent 2, and/or where the heat gun is shutoff when a predetermined safe threshold temperature to the skin 3 of a patient 2 is reached.

For example, FIG. 1 also shows the heat gun HG, having safety locks SL provided therewith, where the nozzle N provides heated air at about 120 to about 130° F. from the concentrated heat source (heat gun HG) through a short tube to the nozzle N for destroying pathogens causing lesions Le in extensive blotches on and under the skin of the patient shown in FIG. 1, such as, for example, from Leishmaniasis pathogens, i.e. protozoa causing cutaneous Leishmaniasis, or other viral and/or idiopathic pathogens causing skin cancers, abnormal pre-cancer dysplasia cells, and which destroy other diseases and pathogens on the skin.

Figure 5:
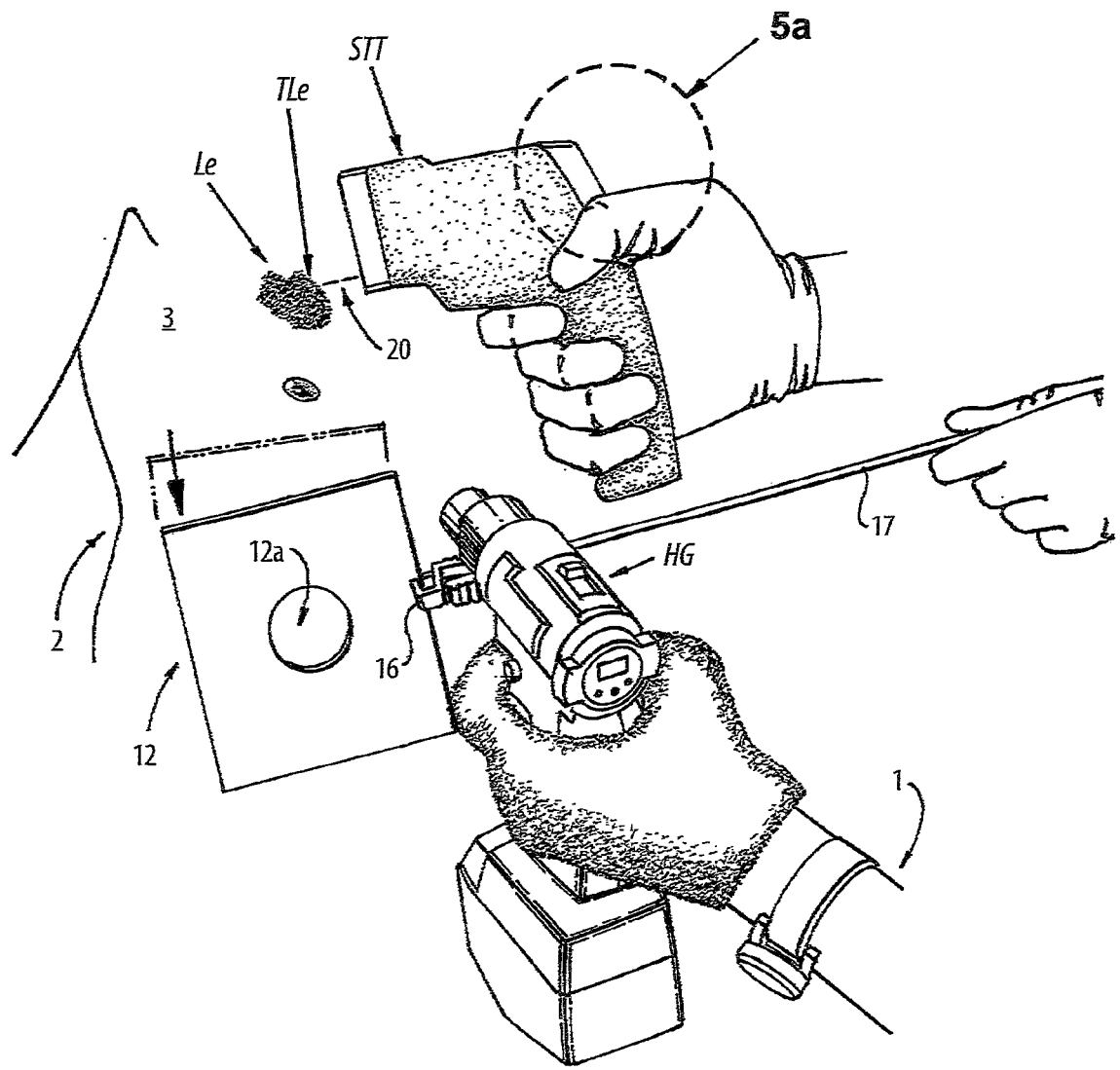
FIG. 5 is a local perspective view, showing the practitioner's hands holding an alternate embodiment for a heat gun, used in connection with a separate handheld non-contact surface temperature measuring device, which remotely measures the actual skin temperature threshold of the skin lesion in situ being measured by a laser infrared light beam, and where the skin lesion is treated by hot air exiting the heat gun at a temperature which renders the skin temperature threshold to be effective in treating the skin lesion.
Figure 5A:
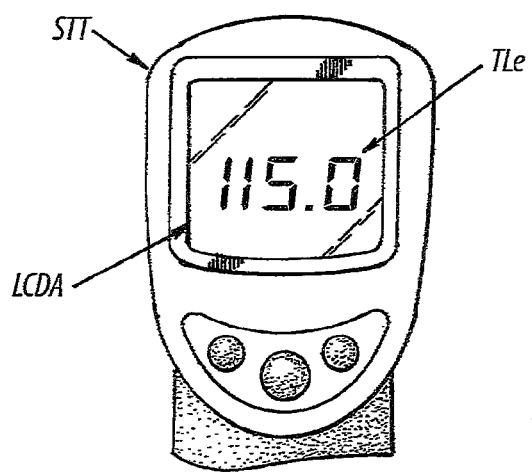
FIG. 5a. is a close-up detailed view of the alternate embodiment of the separate handheld non-contact surface temperature measuring device, taken along dashed view circle line "5a" of FIG. 5, with a single LCD viewing screen, displaying the threshold temperature of the skin lesion being treated.

FIG. 1 also shows a typical heat gun HG, which can have temperature control locks and interlocks SL (such as explicitly disclosed in Applicant's '861 patent and '585 patent, incorporated by reference herein, in its entirety), to keep the outflowing hot air HAEX to cool down to the therapeutic temperature TLe of the skin being treated of about 105° F. . . . 180° F., optionally, in a range of 105° F. . . . 135° F., preferably at about 120° F. to about 130° F. While the LCDA of the heat gun HG displays the programmed temperature of the heated air flow HAF required to achieve the actual required temperature TLe of the skin lesion Le on the skin 3 of a patient 2, to inactivate the pathogen causing the skin lesion Le, can be accurately measured by using a remote portable handheld contactless surface temperature device STT aimed at the actual surface of lesion Le being treated on the skin 3 of the patient 2. Such remote portable handheld contactless surface temperature devices are shown in FIGS. 5 and 5a, such as, for example, manufactured by Berrcom or other similar thermometers using laser infrared signal focused on the skin lesion Le being treated, so that the heat gun can be shut off when the threshold skin lesion temperature TLe is reached, to inactivate and destroy the pathogen which caused the skin lesion to erupt on the skin 3 of a patient 2.

FIG. 2 shows the LCD viewing screen LCDA of heat gun HG, showing the temperature TAEX of the exiting air flow HAF, from the heat gun HG through a nozzle N, pointed at the skin lesion Le on the skin 3 of the patient 2. The LCD viewing screen LCDA displays the temperature of the heat HAEX exiting from the heat gun HG.

FIG. 3 shows the healthcare provider 1 administering heated air HALe to a lesion Le on the skin 3 of a patient 2, where the heat HALe is limited to the area/diameter of a hole 12a on a masking template 12. The hole 12a is configured to be limited to the diameter area LeA of the skin lesion Le. FIG. 3 also shows a plurality of masking templates 12, 13, 14, 15, each having respective holes 12a, 13a, 14a, 15a of varying area sizes, fitting to different sized skin lesions Le, whereby the area of the skin 3 outside of the lesion Le is protected from direct contact with the exiting heat HAEX from the heat gun HG through the nozzle N, before it arrives as heated air HALe, at the preferred temperature TLe of the skin lesion Le, capable of inactivating and destroying the pathogen causing the lesion Le on the skin 3 of a patient 2 afflicted with Cutaneous Leishmaniasis or other skin lesion causing diseases.

FIG. 3a shows clamp 16 holding a masking template 12 of FIG. 3, at the distal end of the clamp 16, and whereby the proximal end (not shown) includes a rod handle 17 for manual or stationary holding of the clamp 16 grasping masking template 12 with hole 12a, while the heat gun HG sends heated air HAEX toward the skin lesion Le, protecting adjacent skin 3 without a lesion Le, by optional masking template 12 with a hole 12a exposing only the skin lesion Le therethrough.

Figure 4:
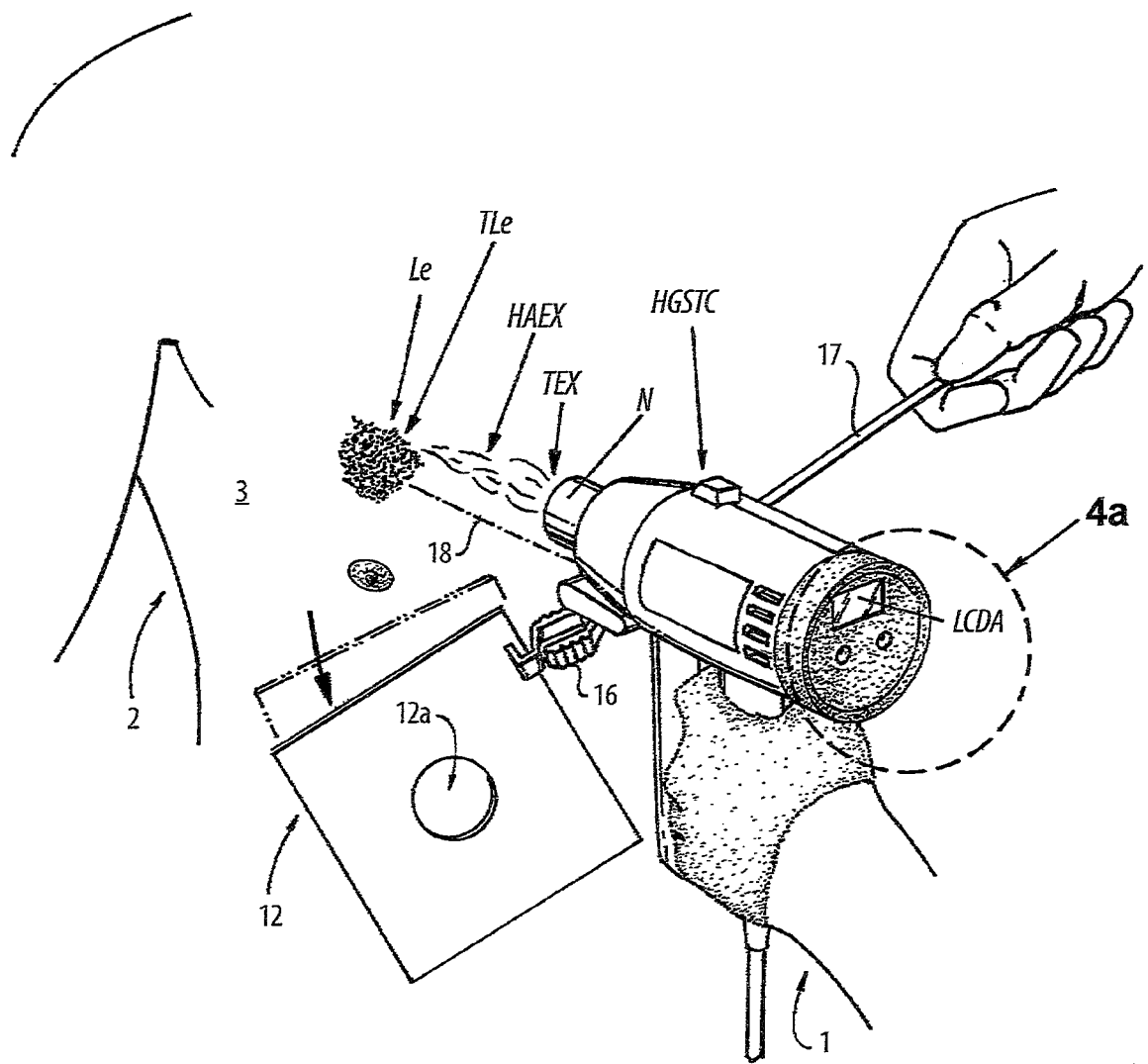
FIG. 4 is a local perspective view, showing the practitioner's hands holding a preferred embodiment for a heat gun, having a built in non-contact surface temperature control (STC), which remotely measures the actual skin temperature threshold of the skin lesion in situ being measured by a laser infrared light beam in real time, and where the skin lesion is treated by hot air exiting the heat gun at a temperature which renders the skin temperature threshold to be effective in treating the skin lesion.

FIG. 4 shows the practitioner 1's hands holding a preferred embodiment for a heat gun HG-STC, having a built in non-contact surface temperature control (STC) operating via laser infrared light beams 18, which remotely measure the actual skin temperature threshold TLe of the skin lesion Le in situ, being measured by the laser infrared light beam 18. preferably in real time (but not required), and where the skin lesion Le is treated by hot air HAEX exiting the heat gun HG-STC, but which, after incidental cooling through the air from the nozzle N of the heat gun HG-STC, arrives at the skin lesion Le at a lowered threshold temperature TLe. The skin threshold temperature, measured remotely by the laser infrared light beams projected on the surface of the skin lesion Le threshold at the skin lesion Le, is effective in treating the skin lesion Le, by inactivating and destroying any pathogen causing the skin lesion Le to proliferate upon the skin 3 of the patient 2. The important threshold temperature TLe is the heated air temperature at the exact location of the skin lesion Le, that renders and inactivates the pathogen causing the lesion Le on the skin 3 of the patient 2.

FIG. 4 also shows a masking template 12 having a hole 12a exposing only the skin lesion Le being treated, where the masking template isolates the unaffected skin 3 of the patient 2 being treated, from heated air from heat gun HG STC, having a built-in non-contact temperature sensing device STT, with an LCD screen LCD-STC, displaying both the temperature the heat gun HG-STC (i.e. shown as 120 degrees F. in FIG. 4a), and temperature Tle at the lesion Le (i.e. shown as 120 degree F.). When the lesion Le is exposed to the threshold temperature TLe, the lesion-activating pathogen is inactivated and destroyed by exposure to the hot air measured as TLe at the lesion Le upon the skin 3 of the patient 2. Such a heat gun HG STC may be a Master Pro-Air STC heat gun corded to 120V AC power. The Master Pro-Air STC is the only currently available Surface Temperature control heat gun in the world. The Master Pro-Air STC is also capable of delivering the heated air flow at gentle air pressures of from about 4 cubic feet per minute (i.e., CFM) to about 8 CFM, or more, up to 16 CFM, as determined the patient's health care practitioner.

While not having a built-in laser infrared thermometer, the programmable Master ProHeat 1400A Digital Professional model can be used in conjunction with a remote handheld non-contact thermometer.

Figure 4A:
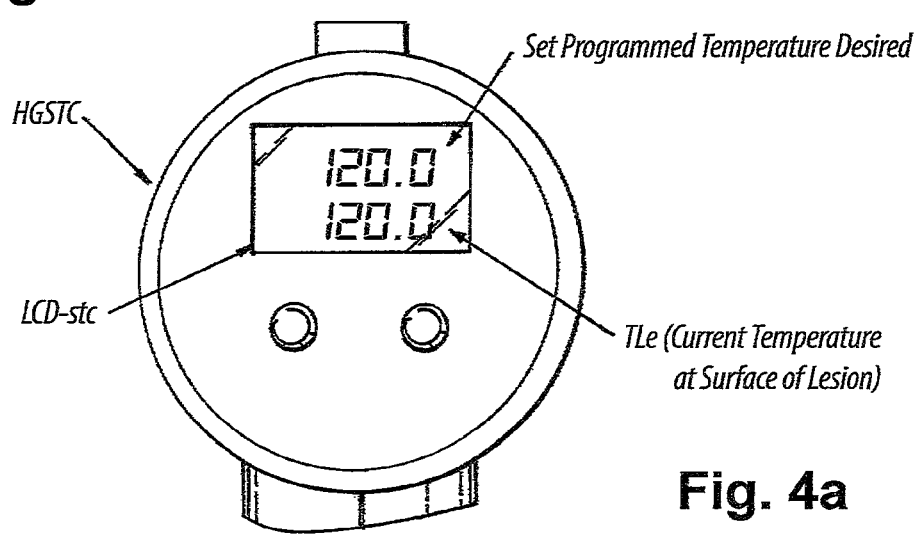
FIG. 4a is a close-up detailed view of the preferred embodiment for a heat gun with a dual LCD viewing screen, taken along dashed view circle line "4a" of FIG. 4, displaying both the target surface temperature selected on the top of the LCD screen, and below, the current moving threshold temperature of the surface being treated on the bottom of the LCD screen.

FIG. 4a shows the preferred embodiment for a heat gun HG-STC with a dual LCD viewing screen LCD-STC, displaying the programmed selected surface temperature on the top of the LCD-STC screen, (i.e. 120 degrees F.), in order to achieve the desired threshold temperature TLe (i.e. 120 degrees F.) of the skin lesion Le being treated, displayed on the bottom of LCD screen LCD-STC.

With respect to use and operation of the Master ProAir STC (identified herein as HG-STC), with a built-in contactless laser infrared temperature thermometer, Applicant incorporates by reference in its entirety, the Instruction Manual thereof, submitted in the Information Disclosure Statement (IDS) filed herein, which discusses the simultaneous use of the heat gun with its built-in contactless temperature thermometer for measuring surface temperatures (being used herein to measure the threshold temperature TLe of the skin lesion being treated, by inactivating and destroying the pathogen which caused the proliferation of the skin lesion Le). The Instructional Manual also discusses choice of nozzles, using a trigger switch and trigger lock, how to operate the gun pressing the trigger switch for the heating element and fan startup, aiming the laser infrared light beams at the target to be measured upon heat application thereto, engaging and releasing the trigger lock, using the PROLOC supervisory key to change between supplying heated air and measuring surface temperature at the lesion Le, and using the surface temperature controls, along with explanatory diagrams associated therewith.

FIG. 5 shows the practitioner 1's hands holding an alternate embodiment for a heat gun HG, used in connection with a separate handheld non-contact surface temperature measuring device STT, which remotely measures the actual skin temperature threshold TLe of the skin lesion Le in situ, being measured by a laser infrared light beam 20 (as shown in FIG. 5a), and where the skin lesion Le is treated by hot air HAEX exiting the heat gun HG and reduced by airflow to a lower threshold temperature TLe at the site of the skin lesion Le, which lower threshold temperature renders the skin temperature threshold TLe to be effective in treating the skin lesion Le. FIG. 5 also shows the healthcare practitioner 1 holding the heat gun HG and a medical assistant holding the separate handheld non-contact surface temperature measuring device STT.

FIG. 5a. shows the alternate embodiment of the separate handheld non-contact surface temperature measuring device STT, as in FIG. 5, with a single LCD viewing screen LCDA, displaying the threshold temperature TLe (i.e. 115 degrees F.) at the skin lesion Le being treated.

Figure 6:
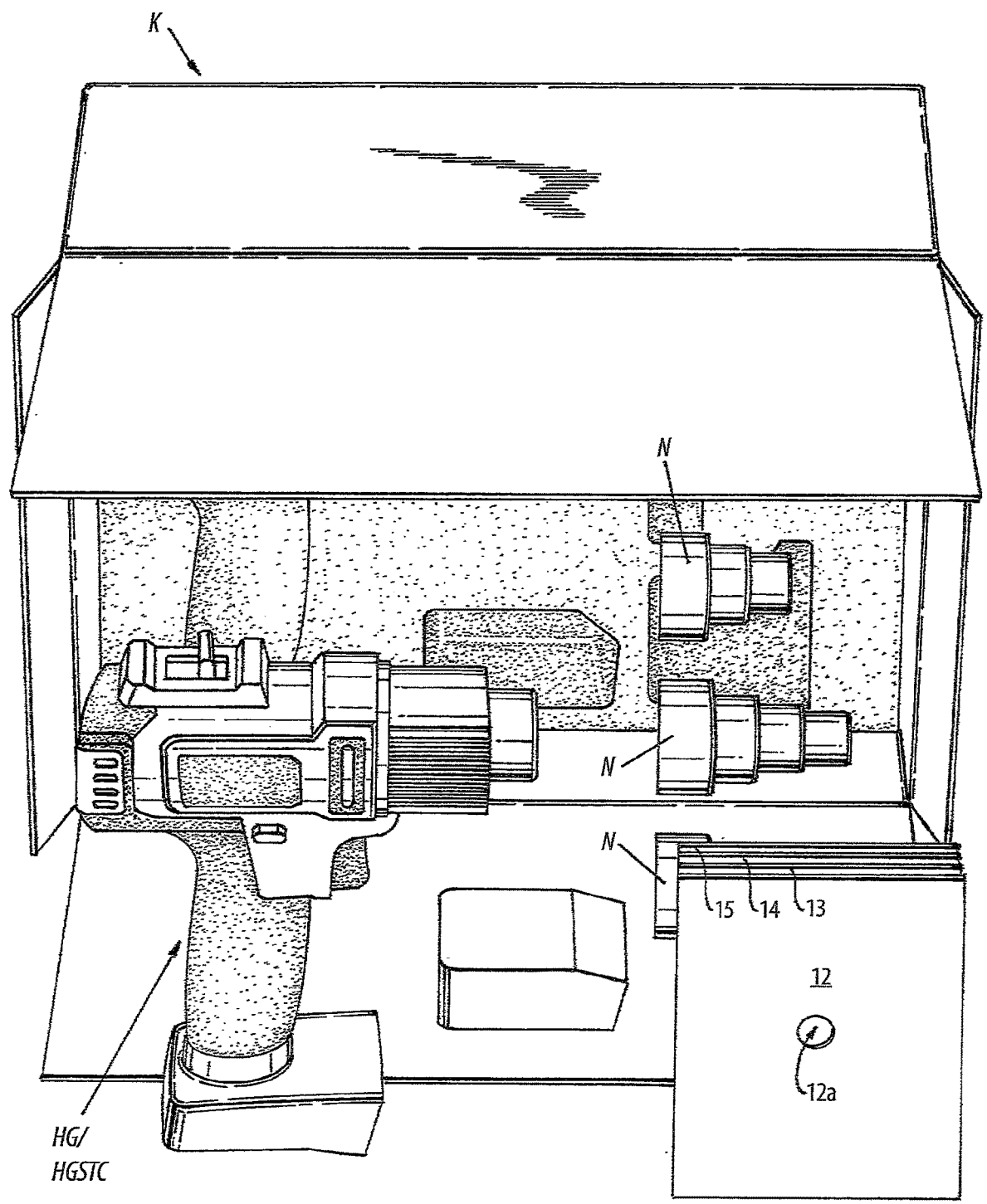
FIG. 6 is a front perspective view of the heat gun of FIG. 1 or 3, provided with a set of nozzles of varying exiting diameters, and a set of masking templates with a set of varying area sizes, fitting to different sized skin lesions.

FIG. 6 shows the heat gun HG or HGSTC of FIG. 1 or 3, provided in a kit K, with a set of nozzles N of varying exiting diameters, and a set of masking templates 12, 13, 14, 15 with a set of varying area hole sizes 12a, 13a, 14a, 15a, fitting to different sized skin lesions Le. If the heat gun HG does not have a remote contactless thermometer, then the kit can be used with a handheld surface thermometer STT, shown in FIG. 5.

It is further noted that preferably the health care practitioner, the patient and/or any assistant may wear protective safety eyeglasses.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. A method of using externally applied topical heat therapy for treating metastatic cancer extending beneath the skin and/or skull of a patient comprising the steps of:
   a) placing a concentrated gentle but efficacious exterior topically applied heated air generated by a heat source adjacent to, and spaced from said cancer extending beneath said skin of said patient, and avoiding all contact with said skin during treatment;

b) directing said gentle but efficacious exterior topically applied heated air from said heat source at said cancer on and/or extending beneath the skin and/or skull of said patient;

c) applying said gentle but efficacious exterior topically applied heated air directed from said heat source to a full area of said cancer extending beneath the skin and/or skull of said patient, without moving said heat source;

d) programming said heat source for producing and directing said gentle but efficacious exterior topically applied heated air to destroy said cancer extending beneath the skin and/or skull of said patient;

e) monitoring said heat source for insuring that said gentle but efficacious exterior topically applied heated air being delivered to said cancer extending beneath the skin and/or skull of a patient does not exceed a predetermined safe temperature threshold of said skin; and, f) mounting a display on or adjacent said heat source showing said set programmed temperature and a current temperature at a skin surface located above said cancer being treated, said cancer located beneath the skin and/or skull of said patient.

2. The method of claim 1, wherein said heat source comprises a heat gun with an outlet nozzle shaped to cover all of said cancer.

3. The method of claim 2, wherein said display comprises an LCD screen showing both of said temperatures, including said set programmed temperature and said current temperature at a surface above said cancer located beneath the skin and/or skull of said patient.

4. The method of claim 3 in which the set programmed temperature is displayed on an upper portion of said screen and a current skin temperature at a surface above said cancer is displayed on a lower portion of said screen.

5. The method of claim 3, using a laser infrared light beam projected on the skin surface located above said cancer for measuring the surface temperature of the skin located above said cancer, to determine the temperature of the cancer located below the surface of the skin or skull of the patient.

6. The method of claim 3, wherein said heat gun has different sized nozzles for different sized cancers.

7. The method of claim 3, wherein said gentle but efficacious exterior topically applied heated air being delivered to said cancer located below the surface of the skin or skull of the patient is in the range of about 107 to 113 degrees F.

8. The method of claim 3 in which a masking template is employed to isolate unaffected skin area from said gentle but efficacious exterior topically applied heated air emanating from said heat gun.

9. The method of claim 2 in which the outlet nozzle of said heat gun is centered over said cancer located below the surface of the skin or skull of the patient.

10. The method of claim 1 in which Lidocaine is administered in a pre-procedural step to anesthetize the skin cancer located below the surface of the skin or skull of the patient and surrounding non-cancerous skin.

11. The method of claim 5 further comprising the step of inserting a subcutaneous needle probe temperature monitor into the in situ site of the tumor beneath the skin being treated and measuring the temperature of the tumor being treated.

12. The method of claim 5 further comprising the step of measuring the surface temperature of the skin located above the cancer, and determining inferentially the temperature of the cancer located below the surface of the skin or skull of the patient.

\* \* \* \* \*